United States Patent [19]

Christenson et al.

[11] 4,041,040
[45] Aug. 9, 1977

[54] ECGONINE DERIVATIVE

[75] Inventors: James Gordon Christenson, North Caldwell; Harvey Gurien, Irvington; Sidney Teitel, Clifton, all of N.J.

[73] Assignee: Hoffmann-La Roche Inc., Nutley, N.J.

[21] Appl. No.: 725,913

[22] Filed: Sept. 22, 1976

[51] Int. Cl.$^2$ .......................................... C07D 471/08
[52] U.S. Cl. .................................. 260/292; 23/230.6; 424/1; 424/1.5; 424/12
[58] Field of Search ......................................... 260/292

[56] References Cited

U.S. PATENT DOCUMENTS 3,498,989  3/1970  Sallay ................................. 260/292

Primary Examiner—Cecilia M. S. Jaisle
Attorney, Agent, or Firm—Samuel L. Welt; George M. Gould

[57] ABSTRACT

A novel derivative of ecgonine is described. This compound, 4-hyroxy-benzoyl ecgonine, is useful as a substrate for iodination with a radioactive isotope of iodine such as $^{125}I$. The resulting radiolabeled compound is useful in a radioimmunoassay for benzoyl ecgonine.

5 Claims, No Drawings

ECGONINE DERIVATIVE

DESCRIPTION OF THE INVENTION

The present invention relates to the novel ecgonine derivative 4-hydroxybenzoyl ecgonine. This compound is readily prepared in a two step process from the known compound ecgonine methyl ester.

In the first step of the process ecgonine methyl ester is reacted with a p-lower alkanoyloxybenzoyl halide at a temperature of from 30° C. to the reflux temperature of the reaction mixture. The reaction can be carried out in any suitable inert organic solvent, preferably in a hydrocarbon solvent, most preferably in an aromatic hydrocarbon solvent such as benzene in the presence of a tri-lower alkyl amine-preferably triethylamine. Preferred p-lower alkanoyloxybenzoyl halides include the p-acetoxybenzoyl halides, most preferably p-acetoxybenzoyl chloride. The reaction product is the corresponding ecgonine methyl ester (p-lower alkanoyloxy) benzoate, i.e., ecgonine methyl ester (p-acetoxy) benzoate which can be isolated in the form of an acid addition salt.

In the second step of the process, the ecgonine methyl ester (p-lower alkanoyloxy) benzoate is selectively hydrolyzed in boiling water to yield the desired 4-hydroxybenzoyl ecgonine. The product can be conveniently isolated in the form of its acid addition salt. Both reaction steps are preferably carried out under an inert gas atmosphere, i.e., under nitrogen.

The term "lower alkanoyloxy" is meant to include radicals derived by removing a hydrogen atom from the carboxyl group of aliphatic monocarboxylic acids having from 2 to 7 carbon atoms, preferably 2 to 4 carbon atoms. Suitable lower alkanoyloxy groups include acetyloxy, propionyloxy, n-butanoyloxy and the like. Acetyloxy is a preferred lower alkanoyloxy.

The term "halide" as used herein is meant to include chloride, bromide, fluoride and iodide. Chloride is a preferred halide herein.

Suitable "acid addition salts" include inorganic acid salts such as the mineral acid salts, i.e., hydrohalide salts such as the hydrochloride, hydrobromide, or hydroiodide; phosphates; sulphates or nitrates; or organic acid salts such as the acetate, fumarate, maleate, formate, benzoate, or the like.

The product of the invention, 4-hydroxybenzoyl ecgonine, is useful as a substrate for iodination with radioactive iodine i.e. $^{125}$I, so as to produce $^{125}$I-4-hydroxybenzoyl ecgonine. This material is useful in conducting radioimmunoassays for benzoyl ecgonine, a metabolite of cocaine. A more complete description of such iodination and the radioimmunoassay procedure is contained in U.S. patent application Ser. No. 725,912, entitled "Radioimmunoassay For Benzoylecgonine", filed of even date herewith, inventor, J. Christenson.

The present invention is further illustrated by the following examples.

EXAMPLE 1

Ecgonine methyl ester (p-acetoxy) benzoate hydrochloride.

Under nitrogen, in a 250 ml flask, were placed 3.21 g (0.016 mole) of ecgonine methyl ester, 115 ml of dry benzene, 3.5 g p-acetoxybenzoyl chloride and 24.7 ml triethylamine. After 18 hr reflux, the mixture was cooled to room temperature, filtered, and washed with benzene, and the filtrate concentrated at reduced pressure to an oil. Treatment of the residual oil with ethereal hydrogen chloride afforded 5 g of product, mp 150° d., 78.2% of theory.

EXAMPLE 2

Ecgonine, 4-hydroxybenzoic acid ester, hydrochloride, hemi hydrate, hemiethanolate.

Under nitrogen 4.3 g of ecgonine methyl ester (p-acetoxy) benzoate was refluxed with 125 ml of water for a period of 18 hours. The cooled solution was made alkaline with sodium carbonate, and extracted with 4×25 ml portions of chloroform. The aqueous solution was then acidified with concentrated hydrochloric acid to pH 6.5 followed by extraction with 7×30 ml portions of chloroform. The aqueous solution was then made acid to pH 2 with concentrated hydrochloric acid, and concentrated to dryness. The residue was slurried in methanol and filtered. Concentration of the methanol filtrate gave 3.1 g of solid which was crystallized from ethanol. The yield of product was 0.85 g, mp 180°–181° d.

$[\alpha]_D^{25} = -72.0°$ (c = 1, methanol).

Additional material obtained from filtrate was 0.9 g. mp 234°–235°. The latter material was shown to differ from the former by differing amounts of solvents of crystallization, but otherwise were identical to each other.

We claim:

1. Ecgonine methyl ester (p-lower alkanoyloxy) benzoate and acid addition salts thereof.

2. The compound of claim 1 which is ecgonine methyl ester (p-acetoxy) benzoate hydrochloride.

3. 4-Hydroxybenzoyl ecgonine and acid addition salts thereof.

4. A process for the preparation of 4-hydroxybenzoyl ecgonine, which process involves selectively hydrolyzing an ecgonine methyl ester (p-lower alkanoyloxy) benzoate or an acid addition salt thereof in water at reflux.

5. The process of claim 4 wherein said ecgonine methyl ester (p-lower alkanoyloxy) benzoate is ecgonine methyl ester (p-acetoxy) benzoate.

* * * * *